Figure 1:
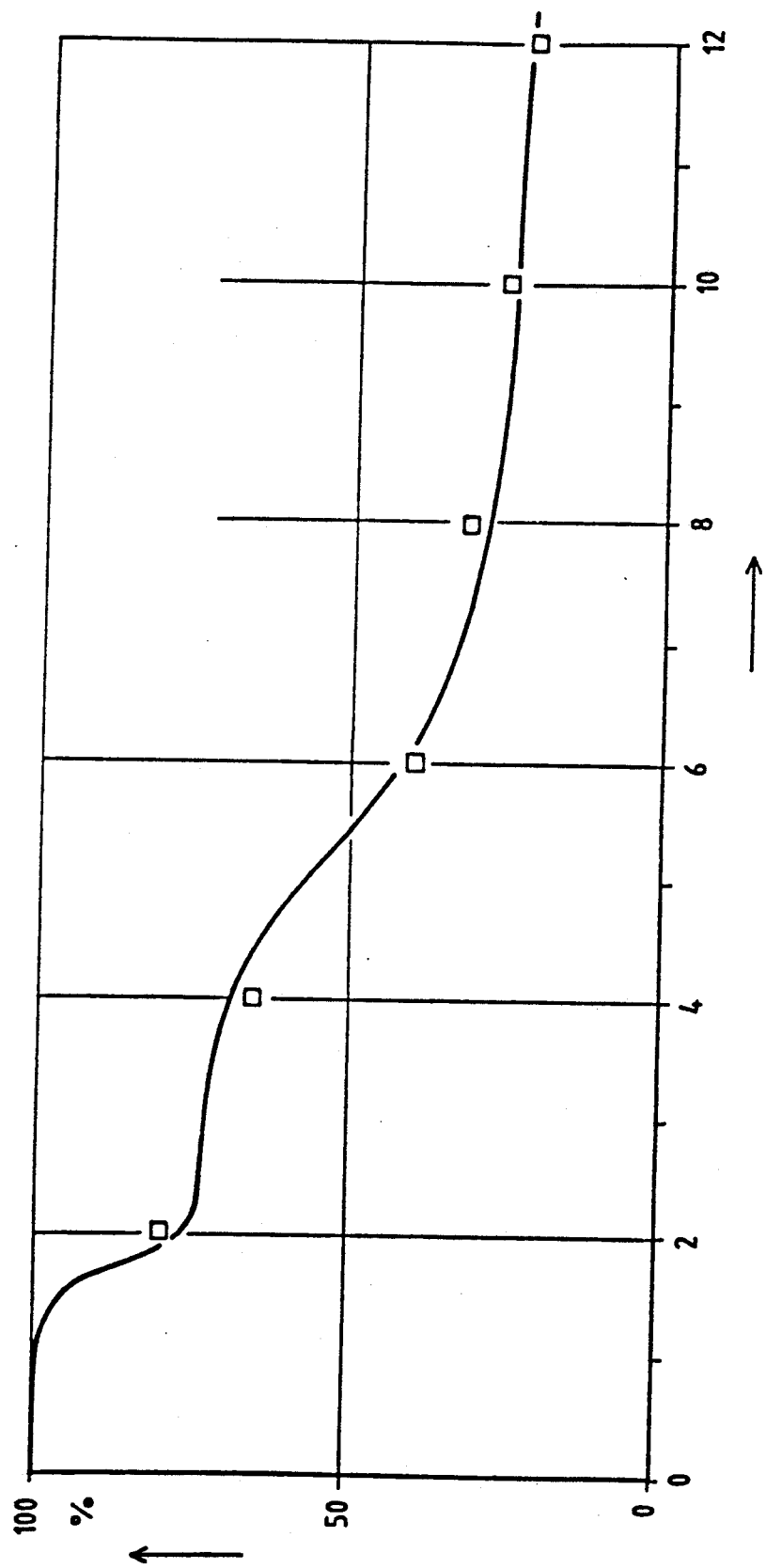

United States Patent [19]

Girrbach et al.

[11] Patent Number: 5,028,736
[45] Date of Patent: Jul. 2, 1991

[54] PROCESS FOR THE SEPARATION AND RECOVERY OF NAPHTHALENE-SULFONIC ACIDS FROM AQUEOUS SOLUTIONS

[75] Inventors: Ulrich Girrbach, Frankfurt am Main; Siegbert Rittner, Mörfelden-Walldorf; Siegfried Bildstein, Kelkheim; Klaus Schmiedel, Königstein, all of Fed. Rep. of Germany

[73] Assignee: Hoechst Aktiengesellschaft, Frankfurt am Main, Fed. Rep. of Germany

[21] Appl. No.: 528,899

[22] Filed: May 24, 1990

Related U.S. Application Data

[63] Continuation of Ser. No. 254,404, Oct. 6, 1988, abandoned.

[30] Foreign Application Priority Data

Oct. 9, 1987 [DE] Fed. Rep. of Germany ....... 3734189

[51] Int. Cl.$^5$ ............................................. C07C 143/24
[52] U.S. Cl. ....................................... 562/89; 562/124
[58] Field of Search ................................. 562/89, 124

[56] References Cited

PUBLICATIONS

Gillette, Chem. Abst., vol. 70 (1969), 33968v.
Bear, Chem. Abst., vol. 102 (1985), 39213w.
Rohm & Haas Company, Amberlite IRA-402 Tech Notes (1961).

Primary Examiner—Alan Siegel

[57] ABSTRACT

The invention relates to a process for the separation and recovery of naphthalenesulfonic acids from aqueous solutions. In this, the naphthalenesulfonic acids are adsorbed on basic ion exchangers and subsequently desorbed again, preferably with the aid of an alkaline liquor, from which the alkali metal sulfonates are then precipitated by cooling.

1 Claim, 2 Drawing Sheets

PROCESS FOR THE SEPARATION AND RECOVERY OF NAPHTHALENE-SULFONIC ACIDS FROM AQUEOUS SOLUTIONS

This application is a continuation of Ser. No. 254,404 filed Oct. 8, 1988, now abandoned.

DESCRIPTION

The present invention relates to a process for the separation and recovery of naphthalenesulfonic acids from aqueous solutions.

Naphthalenesulfonic acids are employed as synthetic building blocks for dyes and as intermediates, for example for $\beta$-naphthol.

It is known that, in the preparation of various mono-, di- and trinaphthalenesulfonic acids, large amounts of effluents are formed which can only be purified or used for the recovery of valuable substances with great difficulty. Since up to now there has been no satisfactory, industrially developed recovery process for naphthalenesulfonic acids from effluents, such effluents are in general fed to a biological processing plant.

Owing to the continuous tightening up of the statutory effluent requirements, it is necessary, in increased measure, to look for purification methods which on the one hand fulfil the statutory conditions and on the other can be operated with a reasonable outlay. Chemical and physical processes for effluent purification such as oxidation, precipitation, flocculation, extraction and adsorption are primarily possible in principle in addition to biological clarification. Purification methods such as oxidations or extractions are mostly expensive and complicated processes. They consume chemicals and lead to losses, because recovery of the valuable substances is no longer possible as a result of chemical degradation.

Liquid-liquid extraction processes using conventional extracting agents such as alcohols or ketones have the disadvantage that naphthalenesulfonic acids cannot be completely extracted even with a large outlay on extraction. Furthermore, the subsequent treatment of the water is unavoidable because of the solubility of the extracting agent in the water. The use of amines as reactive extracting agents, such as is proposed for the preparation of naphthalenesulfonic acids in EP-PS 41,134, is unsuitable for working up naphthalenesulfonic acid-containing effluents since it is complicated in terms of apparatus and costly. The necessary recleavage of the amine-naphthalene-sulfonic acid adducts, for which further chemicals are needed, is disadvantageous here, as well as the difficult regeneration of the expensive amine.

Generally, all known processes are associated with considerable investments of capital and high operating costs.

It has now surprisingly been found that naphthalenesulfonic acids can be separated from various effluents in a simple manner and with low outlay in terms of apparatus and reutilized if basic ion exchangers are used for adsorption. The present invention accordingly relates to a process for the separation and recovery of naphthalene-sulfonic acids from aqueous solutions which comprises treating the solutions with a basic ion exchanger as adsorbent.

The ion exchangers can possess tertiary or quaternary amino groups or groups of the "type I" (trimethylammonium) or "type II" (dimethyl-$\beta$-hydroxyethylammonium) and have gel-like or macroporous structure. The weakly basic, macroporous ion exchanger based on acrylate or polystyrene having tertiary or quaternary amino groups has proved particularly suitable for the process according to the invention.

The regeneration of the loaded ion exchanger and the recovery of the adsorbed naphthalenesulfonic acids preferably takes place by treatment with an alkaline solution, in particular with sodium hydroxide solution, an OH contentration between 2 and 4% by weight of NaOH being particularly suitable. During this, the adsorbed naphthalenesulfonic acid anions are replaced by OH ions and thus pass into the aqueous phase again. Since a substantially lower liquid volume is necessary for desorption than for adsorption, concentration of the naphthalenesulfonic acids in the eluate compared to the original effluent occurs. Precipitation of the naphthalenesulfonic acids from the eluate as alkali metal salts takes place by cooling, preferably to 0° to 5° C. The naphthalenesulfonates precipitated during this can be separated off and further processed. Complete removal of the naphthalenesulfonic acids takes place by feeding back the cooled filtrate into the crude effluent and renewed purification.

Adsorption and desorption can be carried out in the temperature range between $-2°$ C. and $+60°$ C., preferably in the range between 10° C. and 30° C.

The process according to the invention can particularly advantageously be operated continuously. In order to assure continuous operation two adsorption columns can be connected in parallel, for example, adsorption taking place in the one column and the second column being simultaneously regenerated. The effluent is then pumped into the first column where the naphthalenesulfonic acids are taken up by the ion exchanger. The purified effluent is drawn off from the top of the column. The quality of the effluent leaving the column is dependent on the loading state of the ion exchanger and the flow rate in the fixed bed. If the concentration of residual naphthalenesulfonic acids in the purified effluent exceeds a previously stated value after some time, then the column used up till now (first) is switched from adsorption to regeneration position and the second column is employed for adsorption.

To desorb the naphthalenesulfonic acids and regenerate the loaded ion exchanger, dilute alkali metal hydroxide solution, preferably sodium hydroxide solution, is pumped slowly through the fixed bed. The sodium salts of the sulfonic acids can be crystallized out and separated off simply by cooling the eluate.

In particular, the following naphthalenesulfonic acids and their mixtures can be separated using the process according to the invention: naphthalene-1-sulfonic acid, naphthalene-2-sulfonic acid, naphthalene-1,5-disulfonic acid, naphthalene-1,6-disulfonic acid, naphthalene-2,6-disulfonic acid, naphthalene-2,7-disulfonic acid, naphthalene-1,3,5-trisulfonic acid, naphthalene-1,3,6-trisulfonic acid, naphthalene-1,3,5,7-tetrasulfonic acid.

The concentration of the naphthalenesulfonic acids in the effluent to be purified can reach saturation. In addition, the aqueous solutions can contain further dissolved organic or inorganic compounds, where these do not influence adsorption and regeneration. The great advantage of the process according to the invention lies in the high capacity for purification, combined with simple handling of the adsorption and regeneration processes. A further advantage of the process is the low outlay in terms of apparatus which assures substantially problem-free operation.

The following examples more closely illustrate the invention.

The following ion exchangers were used in the examples (Table 1)

TABLE 1

| Ion exchanger No. | Basic framework | Functional groups | Basicity | Obtainable commercially, for example, as |
|---|---|---|---|---|
| 1 | gel-like (polystyrene) | Type II groups | strong | Lewatit ®* M 600 |
| 2 | gel-like (polystyrene) | Type I group | strong | Lewatit ®* M 500 |
| 3 | macroporous (polystyrene) | only tertiary amino groups | weak | Lewatit ®* MP 62 |
| 4 | macroporous (acrylic resin) | tertiary + quaternary amino groups | weak | Lewatit ®* AP 49 |
| 5 | macroporous (acrylic resin) | Type I groups | strong | Lewatit ®* AP 246 |

*Lewatit ® is a trademark of Bayer AG, Leverkusen

EXAMPLE 1-5

10 g of one of the ion exchangers 1 to 5 was added at 25° C. to each 100 g of effluent containing a number of naphthalenesulfonic acids. After 30 minutes, the ion exchanger was filtered off and the effluent was analyzed chromatographically. Table 2 shows the type and content (in % by weight) of the contamination of the effluent before (1st column) and after treatment (2nd to 6th column) and the percentage purification capacity obtained.

TABLE 2

| Example No. | Ion exchanger No. | Naphthalenedisulfonic acids (%) | | Naphthalenemonosulfonic acids (%) | | Naphthalene (%) | Purification capacity (%) |
|---|---|---|---|---|---|---|---|
| | | 1,6-Isomer | 2,7-Isomer | α-Acid | β-Acid | | |
| — (effluent employed) | — | 0.08 | 0.2 | 2.0 | 1.4 | 0.2 | — |
| 1 | 1 | 0.07 | 0.2 | 1.1 | 0.8 | 0.01 | 44 |
| 2 | 2 | 0.06 | 0.2 | 0.7 | 0.5 | 0.07 | 60 |
| 3 | 3 | 0.05 | 0.1 | 0.8 | 0.5 | 0.04 | 62 |
| 4 | 4 | 0.03 | 0.09 | 0.6 | 0.5 | 0.06 | 67 |
| 5 | 5 | 0.03 | 0.08 | 0.5 | 0.5 | 0.07 | 67 |

Up to 67 % of the naphthalenesulfonic acids contained in the effluent could be removed even with 10 % by weight of an ion exchanger.

EXAMPLE 6-8

A flow tube filled with 200 g of ion exchanger was operated as a fixed bed adsorber (diameter of the adsorber 0.018 m, height 1 m). Both the effluent to be purified and, subsequently, the regeneration solution were delivered from below and transported through the adsorber with the aid of a pump. The flow rate was 0.5 m/h.

Figure 2:
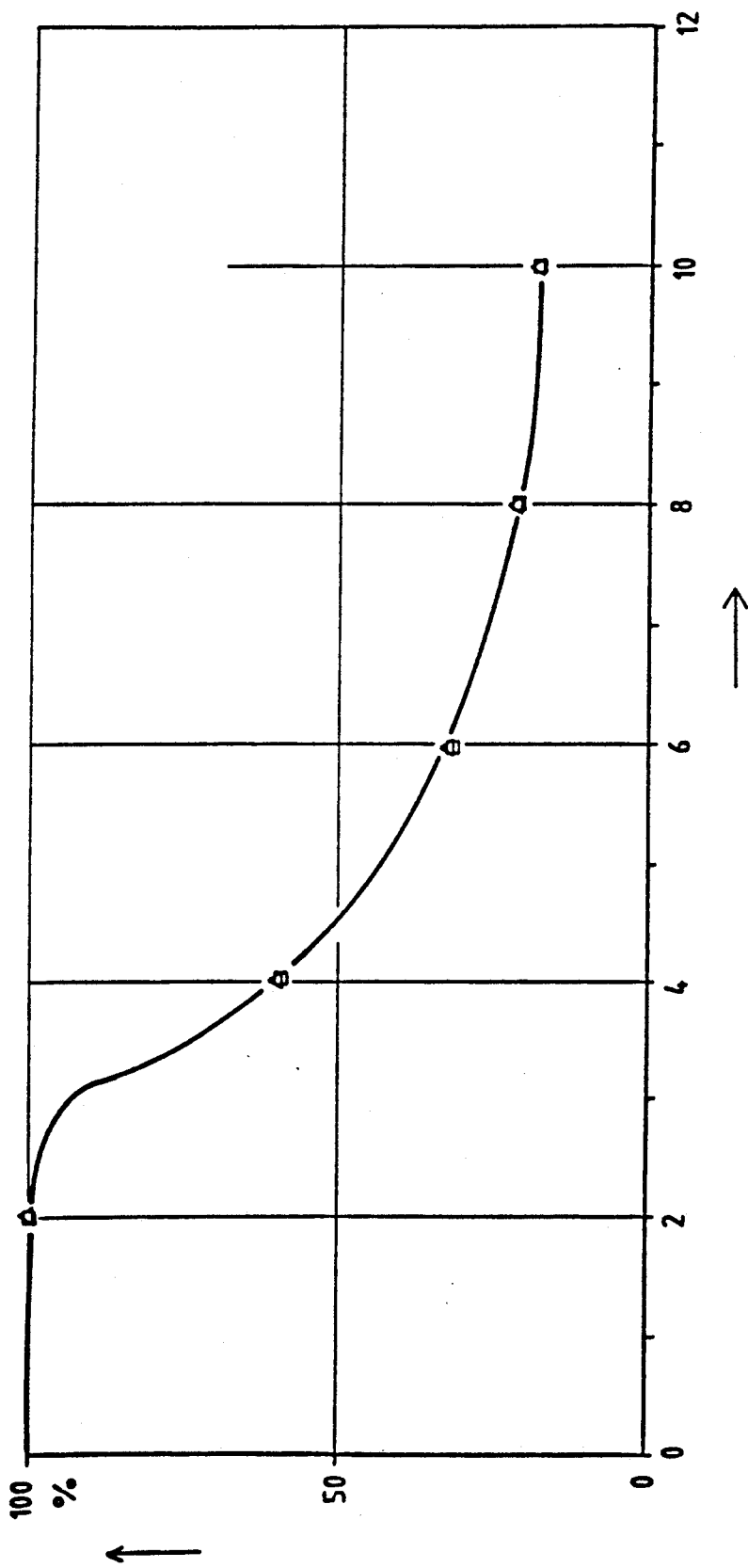

The ion exchangers No. 3 to 5 were tested in succession. In each case, 3 l of effluent of the composition indicated in Table 2 were passed through the adsorber. The break-through curves measured are illustrated in FIGS. 1 and 2. The amount of the effluent pumped through the adsorber has been indicated in this as a multiple of the bed volume.

The regeneration of the fixed bed filled with ion exchanger 3 took place by pumping 1 bed volume of 4 % strength sodium hydroxide solution through the fixed bed and then allowing the sodium hydroxide solution to act for one hour. The eluate was then displaced using 1 bed volume of 4% strength NaOH. To precipitate the sulfonic acids as Na salts, the eluate was cooled to 0° C.

The regeneration of the fixed bed loaded with ion exchanger 4 or 5 took place by carrying out the regeneration step used with ion exchanger 3 five times until the adsorbed naphthalenesulfonic acids were completely desorbed and the ion exchanger could be loaded anew. For reasons of better regenerability, ion exchanger 3 is altogether better suited for the separation of naphthalenesulfonic acids than ion exchangers 4 and 5.

COMPARISON EXAMPLE 1

The process described in Examples 6-8 was carried out using active carbon as adsorbent. It showed that no adsorption of naphthalenesulfonic acids took place.

COMPARISON EXAMPLE 2

The process described in Examples 6-8 was carried out using zeolites as adsorbents (mordenite, ZSM-5, Y). It showed that no adsorption of naphthalenesulfonic acids took place, although the zeolites, as is known, are also ion exchangers.

We claim:

1. A process for the concentration and recovery of a mixture of naphthalenesulfonates from an aqueous solution containing a mixture of naphthalenesulfonic acids, said process comprising:

adsorbing the mixture of naphthalene sulfonic acids in a fixed, basic ion exchange resin bed until said bed is located with the mixture of naphthalenesulfonic acid.

desorbing the mixture of naphthalenesulfonic acids in the form of a corresponding mixture of alkali metal naphthalenesulfonates by treating the bed loaded with the mixture of naphthalenesulfonic acids with an alkaline liquor, thereby obtaining an eluate containing said corresponding mixture of alkali metal naphthalenesulfonates, the volume of resulting eluate being smaller than the volume of aqueous solution from which the mixtures of naphthalenesulfonic acids was adsorbed.

cooling the eluate to 0°-5° C. to precipitate said corresponding mixture of alkali metal naphthalenesulfonates, and separating off the resulting precipitate from the eluate.

* * * * *

UNITED STATES PATENT AND TRADEMARK OFFICE
CERTIFICATE OF CORRECTION

PATENT NO.   :   5,028,736
DATED        :   July 2, 1991
INVENTOR(S)  :   Ulrich Girrbach, Siegbert Rittner, Siegfried Bildstein and Klaus Schmiedel It is certified that error appears in the above-identified patent and that said Letters Patent is hereby corrected as shown below:

In column 1, line 7, "Oct. 8" should be --Oct. 6--.

Claim 1, column 4, line 50, delete "located" and insert --loaded--.

Column 4, line 51, "acid" should be --acids--.

Column 4, lines 51 and 61, delete the periods (".") and insert commas (--,--).

Signed and Sealed this

Twenty-third Day of February, 1993

Attest:

STEPHEN G. KUNIN

Attesting Officer   Acting Commissioner of Patents and Trademarks